(12) United States Patent
Prosl et al.

(10) Patent No.: US 6,451,003 B1
(45) Date of Patent: Sep. 17, 2002

(54) METHOD AND APPARATUS FOR OVERCOMING INFECTION IN A TISSUE POCKET SURROUNDING AN IMPLANTED DEVICE

(75) Inventors: Frank R. Prosl, Middleboro, MA (US); Hans-Dietrich Polaschegg, Kosetenberg (AT); Brian K. Estabrook, Middleboro, MA (US); Klaus Sodemann, Lahr (DE)

(73) Assignee: Biolink Corporation, Norwell, MA (US)

( * ) Notice: Subject to any disclaimer, the term of this patent is extended or adjusted under 35 U.S.C. 154(b) by 83 days.

(21) Appl. No.: 09/640,292

(22) Filed: Aug. 16, 2000

(51) Int. Cl.[7] .............................................. A61M 31/00
(52) U.S. Cl. ...................................... 604/507; 604/265
(58) Field of Search ................................. 604/265, 507, 604/509, 514

(56) References Cited

U.S. PATENT DOCUMENTS

| | | | | |
|---|---|---|---|---|
| 4,676,782 A | * | 6/1987 | Yamamoto et al. | 604/175 |
| 5,344,411 A | * | 9/1994 | Domb et al. | 128/207.14 |
| 5,520,664 A | * | 5/1996 | Bricault et al. | 604/174 |
| 5,741,228 A | * | 4/1998 | Rife | 606/181 |
| 5,782,808 A | * | 7/1998 | Folden | 604/265 |
| 5,820,607 A | * | 10/1998 | Tcholakian et al. | 604/265 |
| 5,853,745 A | * | 12/1998 | Darouiche | 424/423 |
| 5,997,524 A | * | 12/1999 | Burbank et al. | 604/264 |
| 6,287,285 B1 | * | 9/2001 | Michal et al. | 424/422 |
| 6,299,604 B1 | * | 10/2001 | Ragheb et al. | 604/265 |
| 6,299,609 B1 | * | 10/2001 | Finch et al. | 604/502 |
| 6,344,035 B1 | * | 2/2002 | Chudzik et al. | 604/265 |

\* cited by examiner

*Primary Examiner*—William E. Tapolcai
(74) *Attorney, Agent, or Firm*—Burns & Levinson LLP; Frederick C. Williams; Yan Lan

(57) ABSTRACT

An improvement in an implantable port of the type including a housing that is implanted within a subcutaneous tissue pocket is disclosed, wherein the improvement comprises the presence of metallic silver, an inorganic silver compound, a silver salt of an organic acid, or other antimicrobial substances such as taurolidine on the surfaces of the port in contact with, or proximate to, the tissue of said pocket.

9 Claims, 7 Drawing Sheets

METHOD AND APPARATUS FOR OVERCOMING INFECTION IN A TISSUE POCKET SURROUNDING AN IMPLANTED DEVICE

BACKGROUND OF THE INVENTION

1. Field of the Invention

The present invention relates generally to medical implants and to methods for their use. More particularly, the present invention relates to preventing or inhibiting infections internal to the patient in the vicinity of subcutaneously implanted devices or associated with the use of such devices and to configurations of devices that prevent or alleviate localized internal infections. As used herein, the phrase "inhibiting infection" and variations thereof refer to both prophylactic treatment to avoid infection and to therapeutic treatment to eliminate an established infection. More specifically, this invention relates to preventing or inhibiting infections in the vicinity of implanted hemodialysis ports.

2. Description of Related Art

Subcutaneously and transcutaneously implanted devices are utilized for a wide variety of purposes, e.g., drug infusion and hemodialysis access. Heart pacemakers have become commonplace. All such implanted devices are at some risk for infection.

The focus of interest for use of the current invention is hemodialysis access systems for access to human or animal patient's vascular system for high fluid flow rate exchange of blood between the vascular system and an external processing apparatus Various improved access devices have been developed and described in numerous prior art documents.

Such a device is typically a subcutaneously implanted port connected to a blood vessel or other body lumen or cavity usually using a catheter. The port has an aperture for receiving a percutaneous access tube, e.g., a needle. Typical access port apparatuses are disclosed in U.S. Pat. Nos. 5,180,365; 5,226,879; 5,263,930; and 5,281,199.

Ports represent a significant advance over transcutaneous catheters and have a number of common fundamental design features. The ports themselves are made from a variety of materials, e.g., titanium, ceramics, and various plastic materials, e.g., polysulphone, and comprise a housing which forms a reservoir. A surface of the reservoir may be enclosed by a high-density, self-sealing septum, typically made of silicone rubber. Connected to the port housing is typically an implanted catheter that communicates with a vein or other site within the patient where the infusion of therapeutic agents is desired. Implantation of such devices generally proceeds by making a small subcutaneous pocket in an appropriate area of the patient under local anesthesia. The implanted catheter is tunneled to the desired infusion site. When the care provider desires to infuse or remove materials through the port, a hypodermic needle which pierces the skin over the infusion port and docks with the port is inserted.

Recently, improved devices of this class addressing these problems have been developed and described in U.S. Pat. No. 5,954,691 and U.S. patent application Ser. No. 09/083, 078, filed May 21, 1998, the disclosures of which are incorporated herein by reference in their entirety. These inventions are directed to a hemodialysis access system for access to a human or animal patient's vascular system for high fluid flow rate exchange of blood between the vascular system and an external processing apparatus at a volumetric flow rate in excess of 250 ml/minute.

Notwithstanding improvements in the construction of subcutaneous ports, problems still remain that retard their full usefulness in medical practice. Specifically, from time to time infections develop in the capsules or pockets surrounding the implanted devices. Such infections are difficult to treat for the reasons discussed herein and often require the removal of the port or other implanted device.

It is well known that a relatively hard tissue capsule or "pocket" usually forms around an artificial object or device implanted under the skin if the exterior surface of the device is impermeable to tissue in-growth, e.g., where the surface is both hard and non-porous. Pocket formation typically takes place within a few weeks of the implantation of the object in subcutaneous tissue. The capsule, approximately 1 mm thick, forms tightly around the implanted object. Such a capsule is usually white or pinkish and quite slippery to the touch on the inside. The outside of the capsule is attached to the patient's normal subcutaneous tissue. The matrix of the capsule is normally without blood vessels or is very poorly vascularized. When the implanted device comprises a non-porous metal, plastic or elastomer, the capsule usually does not stick or adhere to the artificial material. To a large extent, but not completely, the pocket seals the implanted device off from the surrounding living tissue.

It is also known that infections of subcutaneously implanted ports arise most frequently from skin bacteria transported through the skin by needle penetration. Bacteria, having entered the space between the external surface of the device and the opposed tissue surface, can then attach to the port outer surface and grow into colonies in a layer or film form called biofilm.

While initially localized within the pocket formed around a device, such a colony may not cause symptoms or manifest as an infection for a long time. However, bacteria from the biofilm colony may shed and cross the pocket membrane, whereby an infection will manifest itself. Such an infection can become a local tissue infection indicated by local swelling, pus formation, local heating and pain, and so on, and it can also lead to systemic blood infection. These latter infections are very serious and if not treated often lead to morbidity and ultimately death.

One of the inventors herein, Dr. Sodemann, examined a surgical site at autopsy of a 79 year old patient who had an implanted hemodialysis port for approximately 6 months. There had been no incidents or symptoms which would have suggested an active infection at any time. After autopsy, however, it was found that the outer surface of the implant had been colonized with bacteria. It was concluded that bacteria had not propagated to surrounding tissue outside of the capsule and hence infection had not been suspected.

Infections near a subcutaneously implanted device have frequently been treated by systemic administration of antibiotics after somatic symptoms appear. Often such treatment does not work and the implanted device must be removed, subjecting the patient to additional trauma and leaving the patient without benefit of the device for the time it takes to clear the infection and replace the removed implant with another device. Moreover, the need to administer antibiotics frequently to patients is expensive and patients who suffer from repeated infections often develop strains of bacteria resistant to antibiotics.

Dr. Sodemann conducted a clinical study of a new port for hemodialysis patients, the Dialock®, aided by a proprietary catheter lock solution to prevent infection and clotting inside the indwelling catheter. The method of using the proprietary antimicrobial locking solution in all patients for the first 14 months of the study was to instill the locking solution only in the catheter at the end of a dialysis session and discard it at the beginning of the next session. This study enrolled some 65 patients (the individual implant time ranged from a few weeks to 2 years) for an accumulated experience of approximately 60 patient-years. This study showed an overall infection rate of approximately 0.9 infection episodes per 1000 days of hemodialysis treatment using Dialock® as an access with the proprietary catheter locking solution. The breakdown was approximately 0.1 episodes per 1000 days for blood infections and 0.8 episodes per 1000 days for pocket infection. These infection results compare very favorably with results reported in review papers published in peer reviewed journals, namely, 2 to 10 episodes per 1000 days.

The inventors concluded from the foregoing observations that the risk of pocket infection remained problematic, however. Patients are at risk of having their tissue exposed to bacteria or fungi during each accessing procedure, which usually occurs 3 times a week for the remainder of the patient's life unless the patient receives a successful transplant. Various skin infections abound in dialysis clinics. Studies show that 25–30% of patients and medical staff in hemodialysis clinics are carriers of common pathogens. Bacterial colonization of the surface of the implant inside the capsule has been observed, leading the inventors to conclude that the tissue capsule barrier shields bacteria on the implant surface from the patient's immune system. Thus there is a need for a method of defeating infections around implants inside the tissue pocket.

In the first part of Dr. Sodemann's clinical trial, a substantial number of enrolled patients developed pocket infections. Seven of these patients were treated in the normal manner, namely with systemic levels over a protracted time period of antibiotic specific to the identified bacterium causing the infection. This treatment uniformly failed to eradicate the infections and the implanted devices had to be surgically removed. Immediate removal is the recommended practice because it is very difficult to treat infection from a device that is colonized with a biofilm, and infection that remains in the body will over the long term lead to patient death. Such infections create a dilemma for the patient, who must lose access to renal replacement therapy, which is necessary to sustain the patient's life. Consequently the patient needs to have an alternate access provided and often such patients have exhausted their access sites.

Not satisfied with this situation, Dr. Sodemann began treating his patients with pocket infections in a new way. These patients were systemically infused with antibiotic in the normal manner but were additionally treated with a local bolus of antibiotic at the site of the infection. Dr. Sodemann injected 1 ml of the specific antibiotic directly into the capsule space around the implant. In each of these 12 tissue infections the clinical signs of local infection quickly disappeared. These pocket infections were eradicated and did not reoccur. Thus tissue infections intractable to systemic antibiotic treatment were eradicated using local instillation of antibiotics directly into the inner space of the capsule.

Next it was thought that it might be possible to prevent pocket infections even before they occur. However, it was necessary to determine if one could store an antimicrobial solution within the capsule itself and slow down the normal transport of active ingredients into the circulation which occurs with subcutaneous injection or muscle injection. Accordingly, Dr. Sodemann began a safety experiments to see if a high quantity of antimicrobials could be stored within the capsule. The testing was conducted to determine whether a pathway existed for drug delivery from inside of the intact tissue capsule to the blood stream and the rate of any such drug delivery. He injected a normal loading dose of gentamicin (160 mg per 1 ml saline) into the capsule in patients with implanted access devices. Levels of gentamicin in the patient's bloodstream were measured at 0, 1, 4, 12, 24, 48, and 72 hours after administration.

The measurements indicate a slow uptake in the blood, achieving a very low (non-pharmacologic) bloodstream dose maintained it at steady state over a few days. This means that the capsule is acting as a barrier to rapid uptake into the blood. This steady state level is maintained for a long time. Thus, it appears that the diffusion properties of the capsule acting as a permeable barrier govern the uptake rate. It also suggests that the drug stored inside the capsule does not degrade over the three day measurement period.

Based on these insights, a method was devised to prevent tissue infection. The proprietary catheter lock solution (CLS) is instilled into the catheter in the normal fashion and an additional amount of CLS is flowed into the space between the natural tissue capsule and the implant according to the following procedure.

Syringes were filled with a volume of catheter lock solution determined by the internal volume of the indwelling catheter plus 0.5 ml. After filling of the catheter, the needle was partially retracted so that the tip was resting at the entrance of the implant entrance passage. At this point the remaining 0.5 ml in the syringe was injected into the space at the entrance of the implant so that it flowed into the tissue capsule.

This technique has now been applied clinically for many months with 20 patients. The cumulative experience time is about 5000 days. No infection has occurred in patients to whom this technique was applied. Previous experience would suggest that one should expect about 5 infections. Accordingly, there is a clear desirability to incorporate antimicrobial substances in the pocket around the implanted device.

It is known that certain metals not toxic to the patient in small concentrations have an oligodynamic effect. U.S. Pat. No. 4,054,139 discloses a percutaneous catheter coated with an oligodynamic agent such as metallic silver or its compounds, alone or in association with other heavy metals, such as gold, for the purpose of reducing infection associated with these devices. The oligodynamic agent is typically applied to both interior and exterior surfaces of the disclosed catheters. In another example, U.S. Pat. No. 4,923,450 discloses percutaneous medical tubes having antibacterial action against *Pseudomonas aeruginosa, Staphylococcus aureus, Escherichia coli* and fungus, achieved by means of anhydrous or crystallization-water-containing powdered zeolite, wherein one of the metals contained in said zeolite is substituted by Ag, Cu, or Zn, the zeolite being coated onto or kneaded into at least the portion of said tubes which indwells in the body of the patient. In another example, U.S. Pat. No. 5,295,979 discloses a urinary catheter with a drain lumen coated with oligodynamic metal and with an additional coating of a more noble metal for creating an iontophoretic galvanic couple, which drives antimicrobial ions into solution. The exterior of the catheter is also coated in a similar manner to inhibit microbes migrating toward the bladder along the outer surface of the catheter.

Other inventions use coating of plastics containing antiinfective substances to create infection barriers at crucial points on catheters which penetrate the skin. For example, U.S. Pat. No. 5,567,495 discloses primarily discs or rings that are anti-infective as a result of anti-infective agents impregnated in their surfaces and/or antiinfective activity incorporated into their access sites. The invention is based, at least in part, on the discovery that certain combinations of antimicrobial agents and solvents change the surface characteristics of polymeric medical devices, thereby facilitating the retention of antimicrobial agents. It is further based on the discovery that the incorporation of antiinfective polymeric inserts into the access site of a medical device provides substantially improved antiinfective activity. Similarly, U.S. Pat. No. 5,620,424 discloses an attachable device, for use with a catheter, and impregnated with, or containing, a supply of antiseptic solution, gel or powder, such that the device can be exteriorly positioned adjacent a catheter insertion site, thereby dispensing antiseptic solution at the catheterization site for preventing micro-organisms surrounding the insertion site from causing infection.

U.S. Pat. No. 5,685,961 discloses catheters and other medical devices that include application of multiple layers of metal. In some embodiments, the initial layer of material is silver applied following specific preparation steps. In other embodiments, succeeding layers of metal completely cover the initial layer, and are also of silver. The succeeding layers are deposited over the prior layer, and tend to reduce the incidence of microscopic pores or cracks and are less prone to delamination. The succeeding layers are preferably of mutually different metals between layers. In a particular embodiment, in which the exposed metals are oligodynamic silver and more noble platinum, the exposed silver layer lies over a portion of the platinum layer, to thereby prevent corrosion of the silver layer from disconnecting portions of the silver layer. Fabrication methods include deposition of successive layers by means of sputtering in a longitudinal array of cylindrical magnetron sections, in which each section applies one layer of the coating over the coating applied by the preceding section.

U.S. Pat. No. 5,688,516 discloses compositions and methods of employing them in flushing and coating medical devices. The compositions include selected combinations of a chelating agent, anticoagulant, or antithrombotic agent, with an non-glycopeptide antimicrobial agent, such as the tetracycline antibiotics. Methods of using these compositions for coating a medical device and for inhibiting catheter infection are also disclosed. Particular combinations of the identified substances include minocycline or other non-glycopeptide antimicrobial agent together with EDTA, EGTA, DTPA, TTH, heparin and/or hirudin in a pharmaceutically acceptable diluent. The use of silver sulfadiazine coatings as an antimicrobial agent is also described.

U.S. Pat. No. 5,718,694 discloses a method of inhibiting adherence of bacteria, fungus and other similar microorganisms to the surface of biomaterials, wherein biomaterials, such as catheters and prosthetic devices, are pretreated with a coating of a simple carbohydrate, such as a mono- or di-saccharide. Intravascular catheters treated as such are shown to have significant reduction of adherence by *S. epidermidis, S. aureus,* Candidas and other organisms associated with nosocomial infection.

In general these inventions are directed to preventing infections in patients using percutaneous catheters and other devices with permanent rather than transient skin penetration. In addition, these inventions are directed to disinfection of the lumens of such catheters. What is lacking in the prior art is a method of prophylaxis of infections specifically in a closed pocket surrounding an implanted device where there is no permanent penetration of the patient's skin.

At least one patent publication, WO 99/34852, Brugger, et al. (Jul. 15, 1999) describes the infusion of an antimicrobial substance into the space surrounding an implanted device in order to defeat such infections before they become systemic. Brugger, et al. discloses implanted ports and other devices disinfected by the injection of an antimicrobial agent into a region in the device or in a tissue pocket surrounding the device. In a first embodiment, the antimicrobial agent is injected through an aperture in the device to flush internal regions of the device before infusing the tissue pocket, and flushing outwardly through a tissue tract leading to the device. In other embodiments, the antimicrobial agent is injected directly to a target site on the exterior of the device. Implanted devices may include special, usually hardened, target regions for receiving the sharpened end of a needle used to inject the antimicrobial agent. This method generally requires repeated dedicated injections.

It is therefore an object of the current invention to provide apparatus and method for disinfecting or providing infection prophylaxis with respect to indwelling devices with no permanent fluid connection to the exterior of the patient's skin. It is a further object of this invention to provide means of disinfecting or providing infection prophylaxis of the exterior of implanted devices and the tissue pocket that typically forms around such a device. It is yet a further objective of this invention to provide a system for the use of non-antibiotic antimicrobial substances which do not cause the development of drug resistant strains of bacteria. It is a further objective to provide a system for pocket protection which is cooperative with a system for protecting the lumen of indwelling catheters from infection and clotting.

SUMMARY OF THE INVENTION

In accordance with the present invention, in one embodiment ports and other implantable devices, such as pacemakers and artificial joints, are provided having exterior surfaces comprising an antimicrobial material, whereby bacterial infection in the vicinity of the implanted port is reduced. More particularly, this embodiment is directed to an improved implantable port of the type including a housing that is implanted within a subcutaneous tissue pocket, wherein the improvement comprises the presence of metallic silver, an inorganic silver compound, or a silver salt of an organic acid on the surfaces of the port in contact with, or proximate to, the tissue of said pocket.

In another embodiment, the invention comprises a separate container in the form of a pouch substantially surrounding the implanted device intermediate between the device and the subcutaneous pocket. The pouch, which has antimicrobial properties, is slipped over the device before implantation so as to cover most of the implant surface.

A third embodiment comprises use of a reservoir or depot to hold either an antimicrobial solution or a slurry comprising particles of an antimicrobial substance with low solubility. In one subembodiment this substance can be taurolidine and related substances. In another silver metal or relatively insoluble silver salts may be used. A variation on this embodiment uses an implantable pump which can be periodically refilled.

In a fourth embodiment particularly relevant to hemodialysis, the procedure for withdrawal of the connecting needle is altered so that the needle is at first only partly withdrawn to a predetermined position, whereby a predetermined amount of catheter lock solution can be instilled into the pocket surrounding the device. In a highly preferred version of all of the foregoing, taurolidine or its close chemical relatives or mixtures thereof are used because they are known not to foster development of microbial resistance.

DESCRIPTION OF THE PREFERRED EMBODIMENTS

The present invention provides an improvement to subcutaneously implanted devices comprising means for inhibiting infection in their vicinity. As used herein, the phrase "inhibiting infection" refers to both prophylactic treatment to avoid infection and therapeutic treatment to eliminate an established infection. The methods and apparatus are particularly applicable to disinfection of implanted vascular and other access ports, which are at substantial risk of infection through repeated percutaneous access via needles, access cannulas, stylets, and the like. The improvement of the present invention, however, can also be used in combination with a variety of other subcutaneously implanted devices, including, pacemakers, catheters, prosthetic joints, defibrillators, implantable infusion pumps, and the like. Throughout this disclosure, the same designations numbers are used in different Figures if the region or part so designated is essentially the same in each Figure.

Figure 1:
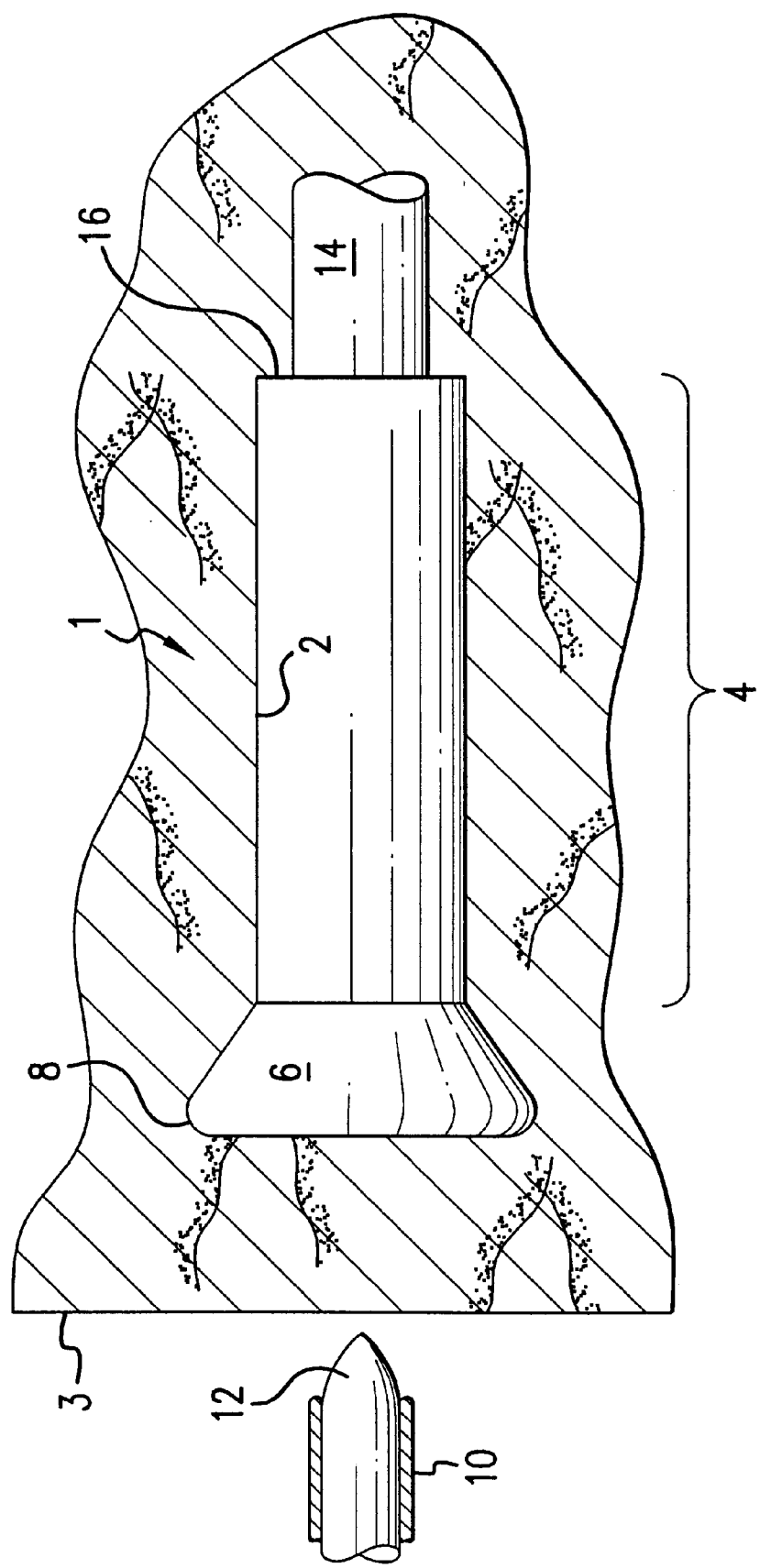
FIG. 1 is a partial cross-sectional schematic view of a hemodialysis access port implanted beneath a skin surface.

FIG. 1 shows a hemodialysis access port 1 implanted beneath a skin surface 3. The port 1 comprises a main body 4 having an outer surface 2, and an access ring 6 having an identification ring 8 that enables an operator to locate the subcutaneous port's entrance when a needle 10, having an obturator 12 is inserted through the skin surface 3 to join with the port 1 by way of the access ring 6. The obturator 12 blocks the movement of tissue fragments into the tip of the needle 10 during insertion of the needle through the skin 3. A catheter tube 14 extends from the distal end 16 of the port 1. The catheter 14 extends into the patient's body, as into a blood vessel or other body lumen or cavity, or solid tissue target site.

While FIG. 1 shows an access port of the sort that would be used in such medical procedures as hemodialysis, the medical devices addressed in the present invention could be any subcutaneously and/or transcutaneously implanted device utilized for a variety of purposes, e.g., drug infusion devices, heart pacemakers and other microelectronic devices as well as artificial joints and the like. All such implanted devices are at risk for infection, especially subcutaneously implanted devices that are periodically accessed by needles and other percutaneously introduced devices. A capsule or pocket of tissue forms about all such implanted devices, and infections can arise in the interfacial region between the inner wall of the capsule and the outer surface of the implanted device.

The most basic embodiment of the current invention is to modify the device itself slightly so that it can be used to flow antimicrobial substances, preferably the catheter lock solution routinely used, into the space between the pocket and the device. This embodiment involves placing an antimicrobial substance in the space between the device and the pocket by flowing an antimicrobial substance into that space. Preferably the antimicrobial substance is a catheter lock solution used in the device. This process is preferably carried out by partially withdrawing a needle used to place the catheter lock solution in the device and providing more catheter lock solution than is needed to fill up the device and attached catheter. The device is configured with an additional flow path hydraulically connected to the main flow path so that partial withdrawal of the needle opens this additional flow path. This additional flow path opens into the pocket so that the extra catheter lock solution can be infused into the pocket.

An alternative embodiment is to infuse substances which are not part of the normal catheter lock into the pocket by the above means or by other means apparent to those skilled in the art. One such substance is polyhexidine.

Figure 2:
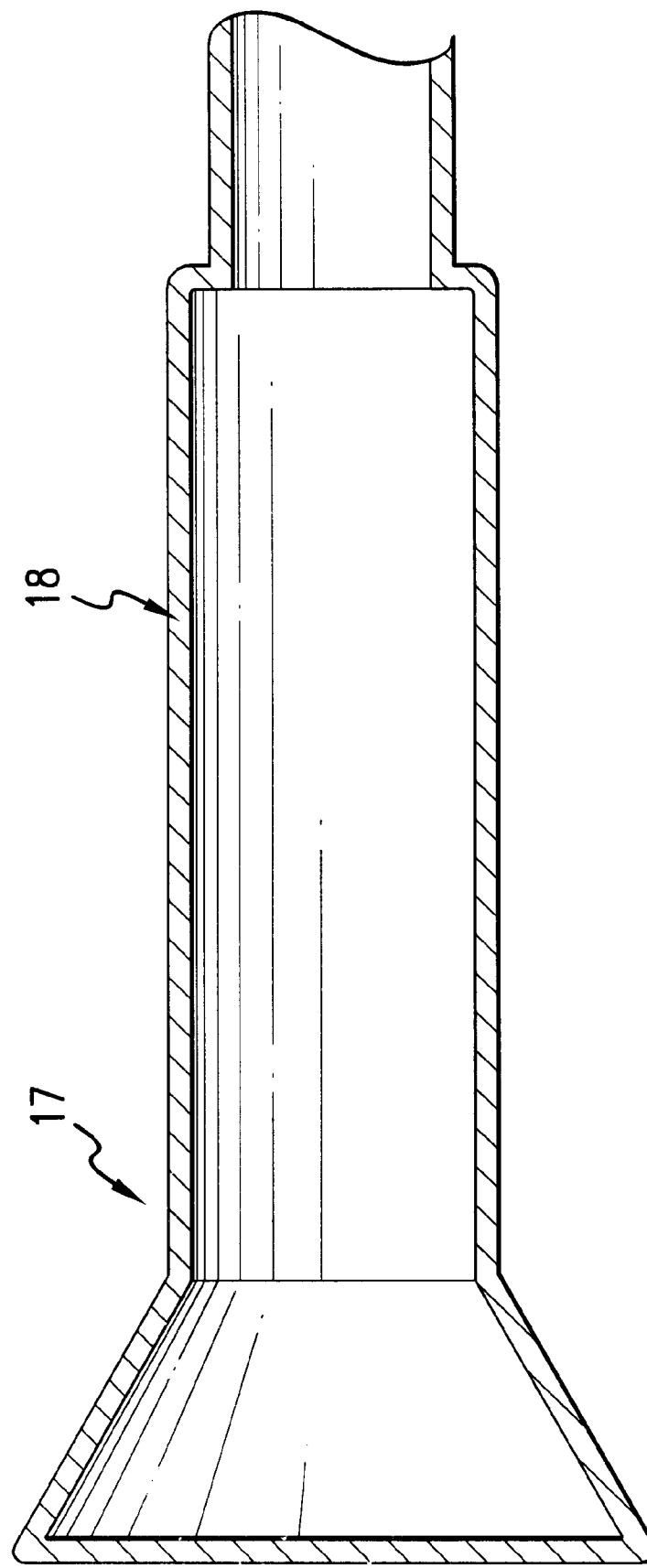
FIG. 2 is a partial cross-sectional schematic view of the port.

FIG. 2 is a partial cross-sectional schematic view of the port 1 of FIG. 1., showing in cross-sectional view the wall 17 of a tissue capsule, or pocket, more or less uniformly disposed about the outer surface of the implanted port. The interface 18 between the capsule wall 17 and the outer surface 2 of the port 1 is the region most prone to the formation of infections. One of the principal objects of the present invention is the inhibition of the growth of bacteria within the interface region 18.

It is known that certain metals and other substances and materials possess antimicrobial properties. One such metal is silver, which has no adverse physiological effects in low concentrations. In a physiological solution silver dissolves slowly and silver ions are formed. In accordance with the present invention, the formation of infection within the capsule or pocket is inhibited by constructing the port from silver or from a pharmaceutically suitable silver alloy or by coating the port with silver, or a silver alloy, or with certain silver compounds. The coating, however, must be sufficiently thick and have sufficient surface area to endure for an intended service life of several years.

Among the silver-bearing materials useful in the practice of the present invention are metallic silver; inorganic compounds, e.g., silver oxide, silver carbonate, or silver nitrate; and salts of silver with organic acids, e.g., silver citrate or silver lactate. Metallic silver is preferred.

The subcutaneous port of the present invention can, if desired, be machined from a solid piece of silver or silver alloy. However, in general, it will normally be preferred to begin with a port constructed of a less expensive material, e.g., titanium, and apply the silver to the external surface by any of several convenient means. For example, silver metal may be applied to the exterior port surface by sputtering, electroless plating, or by other plating methods familiar to those skilled in the art; see, for example, U.S. Pat. No. 5,685,961.

It has been disclosed in U.S. Pat. No. 5,295,979 that experimentation with nutrient broths, which is considered a worst-case condition, has revealed that inhibition of microbes requires about 25 to 50 square millimeters of silver surface per milliliter of broth. Conventional plating techniques may not provide a surface area of this magnitude. Thus, in the practice of the present invention, it is highly desirable to maximize the surface area of the silver. One way to maximize available surface area for a given quantity of metal is to incorporate very small particles of silver, e.g., silver particles in the micron or sub-micron range, into the surface of the implanted device. Another method by which to increase the exterior surface area of the port is by grooving or roughening of the surface, as by grit blasting or etching, so as to increase the exposed area upon which silver may be deposited. Alternatively, very finely divided silver particles may be attached to the exterior surface of the port by any suitable means, such as by coating, wherein the particles are dispersed in a polymeric matrix that will adhere to the exterior surface of the port.

A coating may be formed with, for example, a proteinaceous matrix or a matrix form of such organic plastics as polyethylene, polypropylene, polyvinyl chloride, polytetrafluoroethylene, polyurethane, or silicone. If this is done, it will normally be advantageous to maximize the silver/polymer weight ratio in the coating, in order to maximize the quantity of particles of metallic silver or silver compound that are exposed to the exterior. Typically, such a result can be realized by dispersing the particles in a dilute solution of the polymer in a suitable solvent, applying the mixture to the port by conventional methods, such as brushing, spraying, or dipping, and then evaporating off the solvent.

Another means for applying a coating of finely divided metallic silver to the exterior surface of the port would be analogous to the preparation of a photographic negative. In such a method, a conventional photographic emulsion of silver halide, e.g. silver chloride or silver bromide, would be prepared and applied to the exterior of the port, usually in the dark. The coated port would then be exposed to light and subjected to the reducing action of a conventional photographic developer. The result would be a thin layer of metallic silver of high surface area deposited on the exterior of the port.

Krall, et al. have described at least two additional methods of applying oligodynamic substances to plastic parts to be used in the body. In U.S. Pat. No. 5,516,480, issued May 14, 1996, Krall and Guggenbichler disclose a method of preparing plastic parts that cannot be colonized by germs and fungi. In this method, the plastic part is first shaped for its intended use. Then a swelling agent, such as acetone or ammonia, is applied to the external surfaces. Then the part with swollen surfaces is then immersed in a non-water based solution of an oligodynamic substance, such as silver chloride, such that the silver chloride is absorbed preferentially in the swollen portion. The swelling agent and the solvent then evaporate, leaving a layer on the treated surfaces containing an effective oligodynamic substance. In another method devised by these same inventors, objects for use in medical applications are made from treated plastic. This treated plastic is formed by taking a plastic blank of the appropriate substance and depositing a thin film of oligodynamic substance, for example metallic silver, on the surfaces of the blank. After deposition the blank is pulverized and, in one embodiment, the resultant powder is melted and formed into the desired shape for the medical device. Parts so formed have oligodynamic effect.

Other methods of applying an oligodynamic coating to the exterior of the port or to the body of the material from which the port is made will be apparent to those skilled in art from the above description.

In a highly preferred embodiment of the present invention, the silver comprises the exterior of a port of the kind described in U.S. Pat. No. 5,954,691 and U.S. patent application Ser. No. 09/083,078, filed May 21, 1998. The preferred port for use in the practice of the present invention is, thus, an implantable, subcutaneous access device suitable for applications requiring flow rates of 250 mL/min or greater, with low pressure drops along a streamlined flow-path having substantially no stagnation points.

Figure 3:
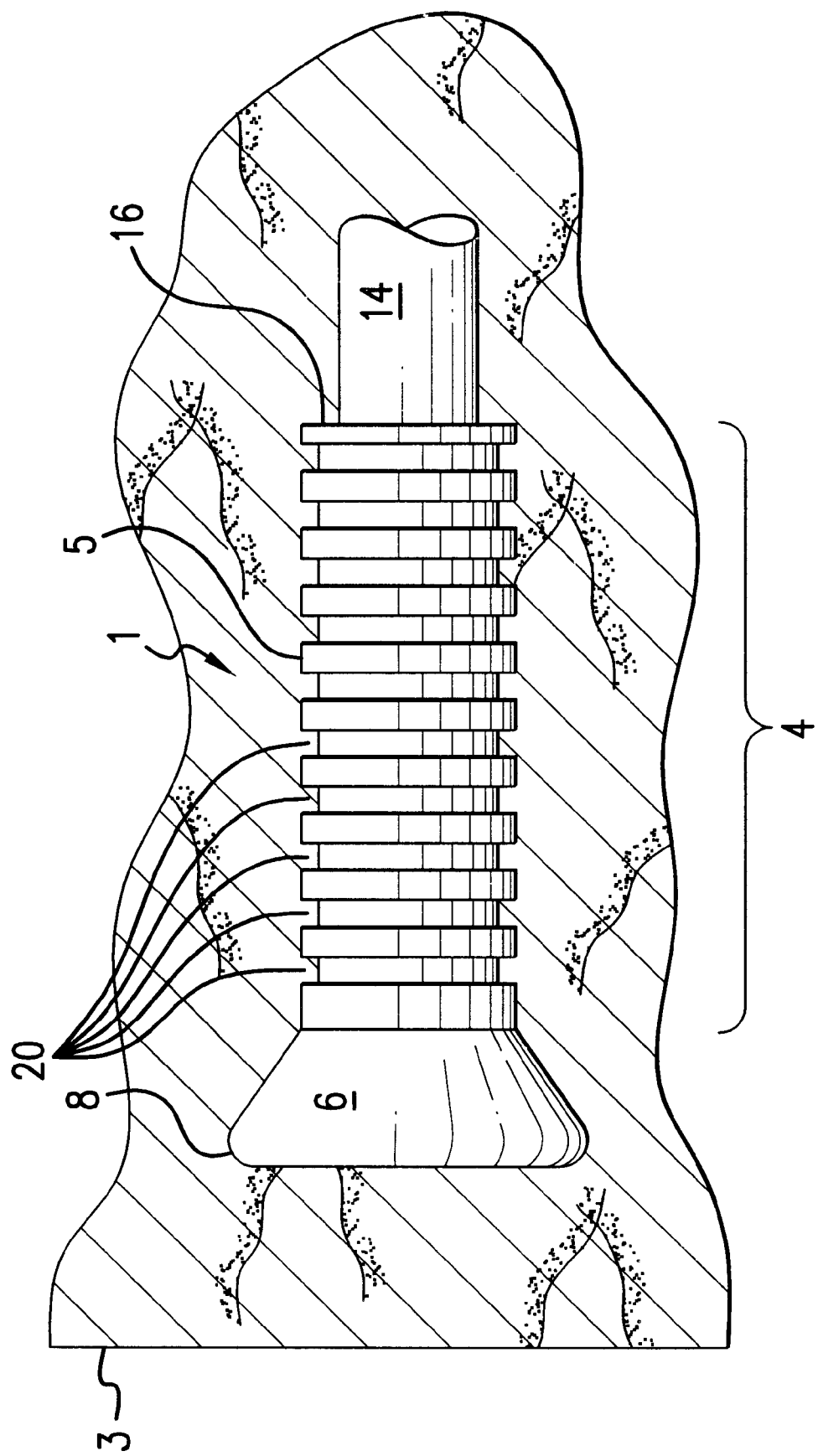
FIG. 3 is a different cross-sectional schematic view of an implanted hemodialysis access port.

FIG. 3 is a partial cross-sectional schematic view of an implanted hemodialysis access port 1 of the sort shown in FIG. 1. The port 1 is implanted beneath a skin surface 3. A cylindrical portion 5 of the main body 4 is shown having circular grooves 20, which serve to provide an increased total surface area from which silver ions are able to diffuse into the interfacial space between the main body 4 of the port 1 and a surrounding tissue capsule (not shown).

The plurality of circular grooves 20 are but one example of a means by which to increase the external surface area of the implanted access port 1 or other implanted medical device. Knurling, etching, or grit blasting or other methods of increasing the surface area are also within the spirit and scope of the present invention.

Figure 3A:
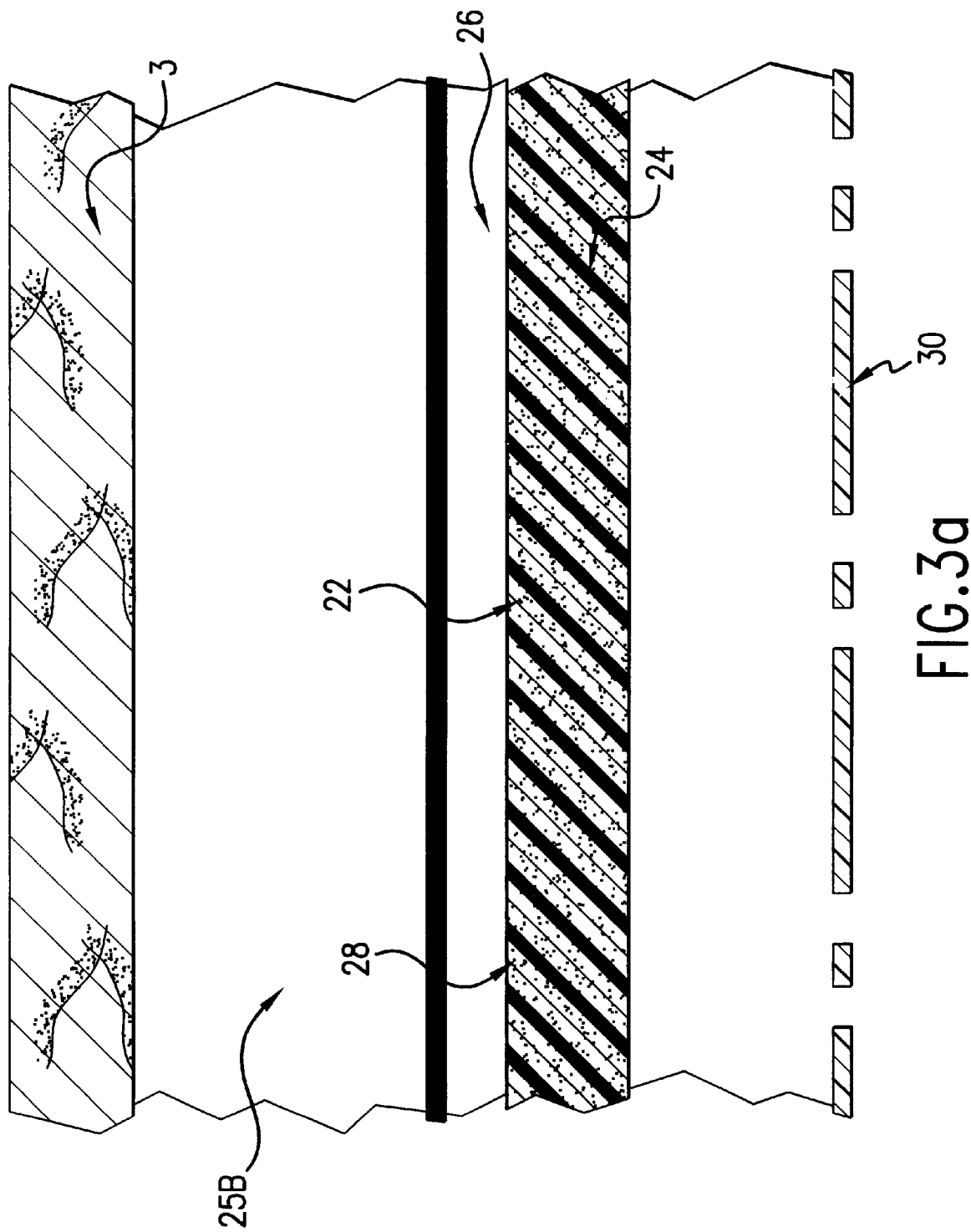
FIG. 3a is a close-up cross-sectional view of metallic silver particles embedded in a polymeric matrix material.

Alternatively to the use of machined grooves or other aforesaid methods by which to increase the external surface area of implanted devices, the inventors conceive that finely divided silver particles may be attached to the exterior surface of the port by any suitable means, such as by coating, wherein the particles are dispersed in a polymeric matrix that will adhere to the exterior surface of the port. FIG. 3a is a close-up cross-sectional view of metallic silver particles 22 embedded in a polymeric matrix material 24. The inventors envision the silver-filled polymeric layer 24 to provide the requisite large surface area of metallic silver particles 22. The inventors also feel it is within the scope and spirit of the present invention that the matrix-imbedded particles 22 could as well be low-solubility organic or inorganic salts of compounds of silver or other solid-phase antimicrobial material which yields up its antimicrobial factors into the interfacial space 26 between the external surface 28 of the implanted device and the inner wall 30 of the surrounding capsule 32.

More specifically with regard to the matrix material 24 of such coatings filled with silver or related solid-phase antimicrobial materials, they may be formed of, for example, proteinaceous materials or from such organic plastics as polyethylene, polypropylene, polyvinyl chloride, polytetrafluoroethylene, polyurethane, or silicone rubber. It will normally be advantageous to maximize the silver/polymer weight ratio in the coating in order to maximize the quantity of particles of metallic silver or silver compound that are exposed at the exterior surface of the device. Typically, such a result can be realized by dispersing the particles in a dilute solution of the polymer in a suitable solvent, applying the mixture to the port by conventional methods, such as brushing, spraying, or dipping, and then evaporating off the solvent.

Another means for applying a coating of finely divided metallic silver to the exterior surface of the port would be analogous to the preparation of a photographic negative. In such a method, a conventional photographic emulsion of silver halide, e.g. silver chloride or silver bromide, would be prepared and applied to the exterior of the port, usually in a dark setting. The coated port would then be exposed to light and subjected to the reducing action of a conventional photographic developer. The result would be a thin layer of metallic silver of high surface area deposited on the exterior of the port. Other methods of applying a silver coating to the exterior of the port will be apparent to those skilled in art from the above description.

In a highly preferred embodiment of the present invention, the silver comprises the exterior of a port of the kind described in U.S. Pat. No. 5,954,691 and U.S. patent application Ser. No. 09/083,078, filed May 21, 1998. The preferred port for use in the practice of the present invention is, thus, an implantable, subcutaneous access device suitable for applications requiring flow rates of 250 mL/min or greater, with low pressure drops along a streamlined flow-path having substantially no stagnation points. FIGS. 1, 2 and 3 show, in partial cross-sectional schematic view, such an implanted subcutaneous access device 1.

An alternative embodiment of the aforesaid '691 access port device, a pouch having antimicrobial properties substantially surrounds the implanted device. More specifically, the pouch in is fabricated substantially from a material that contains an antimicrobial substance dispersed throughout the material.

A related embodiment involving a pouch envisions the pouch as having a tube-like form that surrounds the access port and contains a solid antimicrobial substance within a skin permeable to water-based body fluids and to water-dissolved antimicrobial substance or substances. That is to say, the water-based body fluids can leach small amounts of the antimicrobial substance into the interfacial space between the inside of the tissue capsule and the outer surfaces of the pouch surrounding the implanted device. Examples of such antimicrobial substances that can be contained within the pouch are metallic silver, silver compounds, and taurolidine which is available in solid form with known anti-microbial properties. Examples of the material from which the pouch can be made are silicone rubber, polyurethane, and the like.

Figure 4:
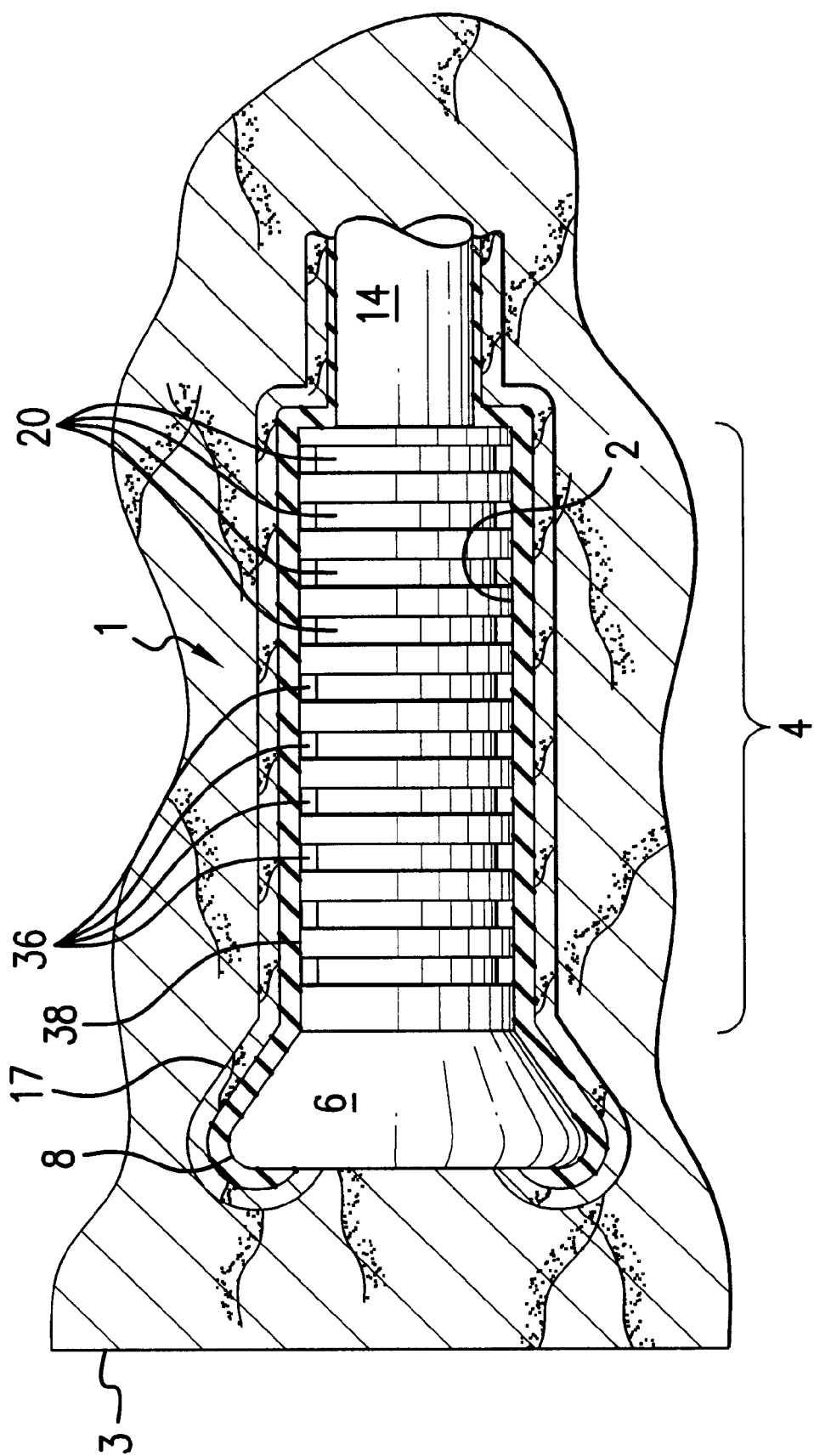
FIG. 4 is a different view of the same kind of generalized implanted device as in the previous drawings.

FIG. 4 shows the same kind of generalized implanted device 1 as in the previous drawings. More specifically, the access port 1 has cylindrical grooves 20 of the sort shown in FIG. 3. However, in this example, the outer surface 2 of the access port 1 is covered with a snug-fitting pouch 34 made of permeable material such as silicone rubber, polyurethane rubber, ore material with micropores, such as dialysis membranes (polysulfone and cellulosic membranes), and the grooves 20 are filled with an antimicrobial substance 36 in solid, liquid or paste form. The antimicrobial substance 36 is free to dissolve in water-based body fluids that penetrate the material of the pouch 34 and thence be defused radially outward into the interfacial space 38 between the radially outwardmost surface of the pouch 34 and the inwardmost surfaces of the tissue capsule 17. Accordingly, the inventor (s) envision that the interfacial region 38 will maintain an antimicrobial solution of sufficient strength to inhibit the formation of infections around the main body 4 of the implanted device 1. Notice further in FIG. 4 that the pouch 34 extends over the main body 4 of the implanted device 1, but does not include the catheter 14 to which the port 1 provides access in the specific instance of this example.

Figure 5:
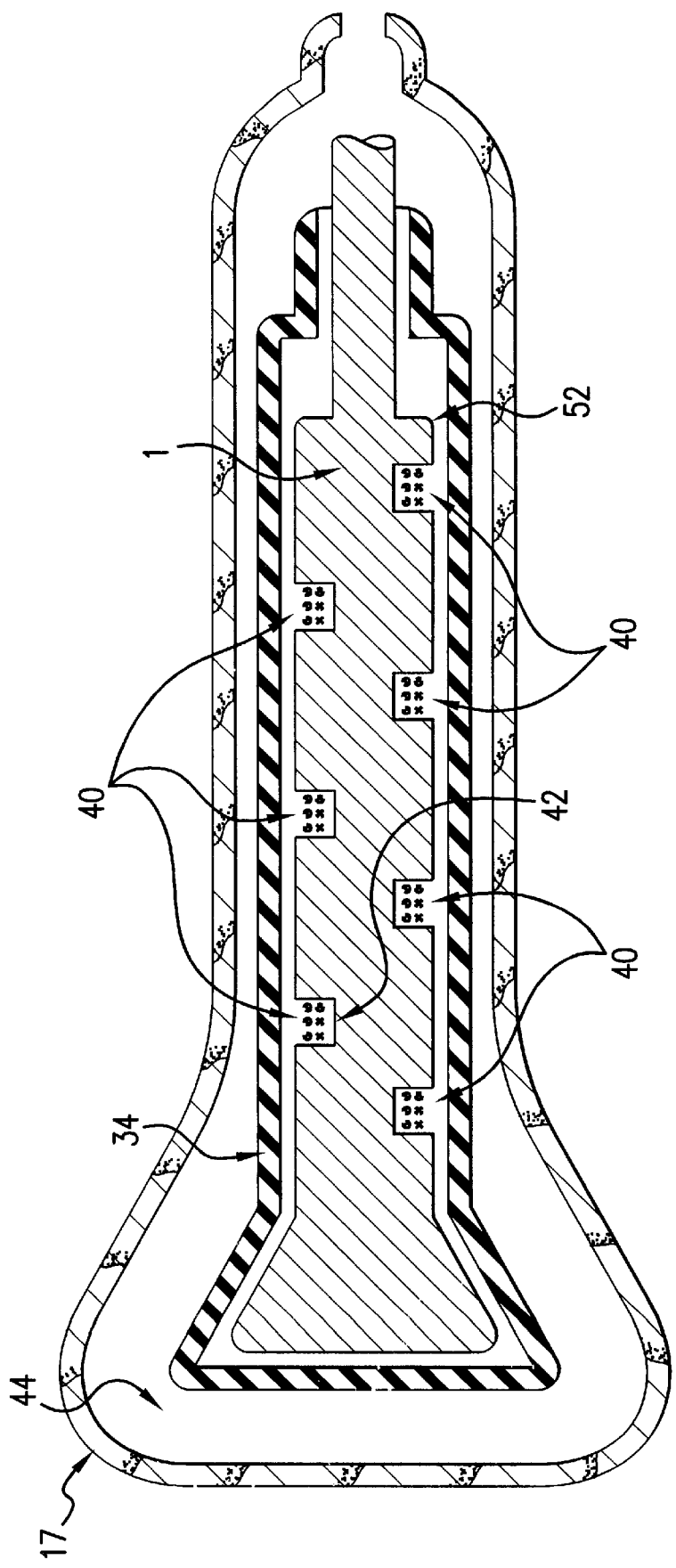
FIG. 5 is yet another embodiment in which a pouch made of permeable material surrounding an implanted device.

FIG. 5 is yet another embodiment in which a pouch 34, made of permeable material and similar to that in principle to the pouch illustrated in FIG. 4 surrounds an implanted device 1. The antimicrobial material 40 is held, in solid, liquid or paste form, within regularly or space indentations 42. As in the embodiment in FIG. 4, the antimicrobial substance 40 is free to interact with water-based body fluids and thus defuse into the interfacial space 44 defined by the inner wall of the tissue capsule 17 and the outer surface of the pouch 34 surrounding the implanted device 1. FIG. 5a is a close-up view of one of the indentations 42 of FIG. 5. Antimicrobial material 40 is contained within the indentation, beneath the pouch 34, through which the antimicrobial material, in water solution, is free to defuse into the interfacial volume 46 defined by the inner surface 48 of the tissue capsule 17 and the outer surface 50 of the pouch 34. Examples of such antimicrobial substances 40 that can be contained within the pouch 34, adjacent the outer surface 52 of the implanted device 1 are metallic silver, silver compounds, and taurolidine, a substance available in solid form with known anti-microbial properties.

The inventors yet further envision that the pouch idea illustrated in FIGS. 4, 5, and 5a might be used in conjunction with a variety of antimicrobial storage means, other than the cylindrical grooves 20 and the indentations 42. For example, a grit-blasted surface or one that has been etched into a specifically advantageous shape would conceivably be able to hold and store sufficient amounts of adequately water-soluble antimicrobial substance to maintain an interfacial space between the inner surface of a tissue capsule and the outer surface of a pouch with an adequate supply and concentration of antimicrobial activity for the designed service life of the implanted device.

Figure 6A:
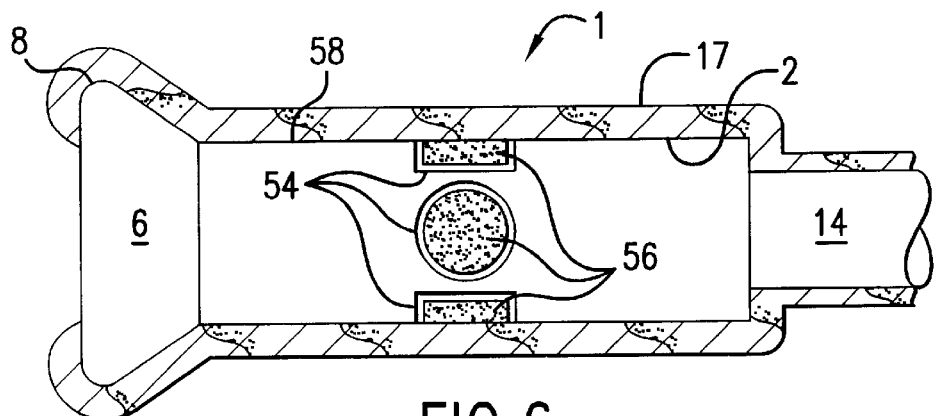
FIG. 6a illustrates yet another embodiment of the present invention showing the subcutaneously implanted access port surrounded by a tissue capsule.
Figure 6B:
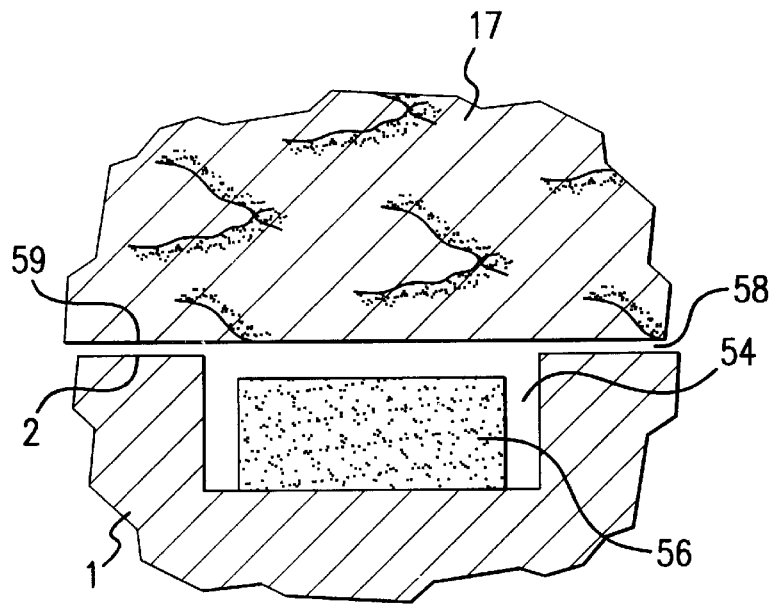
FIG. 6b is a close-up cross-sectional view of one of the volumes containing the antimicrobial material.

FIG. 6a illustrates yet another embodiment of the present invention. Once again, as in the previous figures, the implanted device shown schematically is an access port, though the basic anti-infection principles presented herein can be applied to any number of subcutaneously implanted medical devices. In FIG. 6a, the subcutaneously implanted access port 1 is shown surrounded by a tissue capsule 17. Provided in the outer surface of the access port 1 are a plurality of volumes 54 each of which contains an antimicrobial material 56. The antimicrobial material 56 is preferably a solid having adequate solubility and water-base body fluids to maintain a layer of antimicrobial solution of adequate concentration in the interfacial volume 58 separating the tissue capsule 17 from the outer surface 2 of the implanted device 1. However, while the antimicrobial material 56 is shown in FIG. 6a as being a solid, the inventor(s) anticipate that suitable antimicrobial gels or salves, having the appropriate solubility in body fluids, can also be used. FIG. 6b is a close-up cross-sectional view of one of the volumes 56 containing the antimicrobial material 56. Water-based bodily fluids interact with the antimicrobial material 56 so as to maintain an antimicrobial solution of adequate and long-term concentration within the interfacial void 58 separating the outer surface 2 of the implanted device 1 from the inner wall 59 of the tissue capsule 17.

Figure 6C:
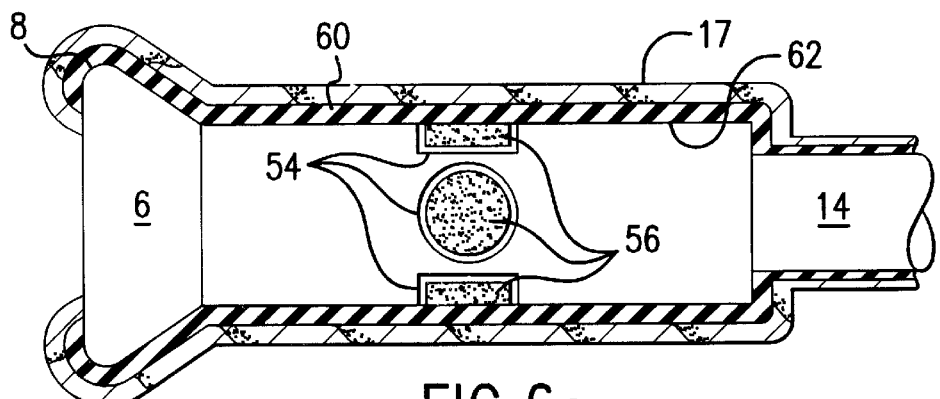
FIG. 6c is an embodiment in which a permeable pouch is shown surrounding the implanted device.

FIG. 6c is an embodiment in which a permeable pouch 60 is shown surrounding the implanted device 1. Antimicrobial material 56, stored in the recesses 54 dissolves in bodily fluids that defuse through the pouch 60 and which subsequently migrate to the outside of the pouch, conveying an antimicrobial solution into the interfacial region defined by the outer surface 62 of the pouch 60 and the inner surface of the tissue pocket 17.

In the alternative embodiment of a pouch with antimicrobial properties substantially surrounding the implanted device, the pouch in one subembodiment is fabricated substantially from a material that contains an anti-microbial substance dispersed throughout the material. In another sub-embodiment, the pouch comprises a tube-like form which surrounds and contains a solid anti-microbial substance within a skin permeable to water and to the anti-microbial substance in solution such that the water can leach small amounts of the anti-microbial substance into the fluid between the pocket and the implanted device. Examples of such substances are metallic silver, silver compounds, and taurolidine, a substance available in solid form with known anti-microbial properties.

It will now be apparent to those skilled in the art that other embodiments, improvements, details and uses can be made consistent with the letter and spirit of the foregoing disclosure and within the scope of this patent, which is limited only by the following claims, construed in accordance with the patent law, including the doctrine of equivalents.

We claim:

1. A process for disinfecting and rendering inhospitable to infections the space between an implanted device and encapsulating tissue which forms around the device, said process comprising the step of applying an antimicrobial substance to the external surface of the implanted device in a configuration such that the antimicrobial substance is able to leach into said space.

2. The process of claim 1 wherein the step of applying the antimicrobial substance to the external surface of the implanted device is performed by a process chosen from the group plating, electroless plating, and sputtering.

3. The process of claim 1 comprising an additional step inserted before the applying step, said additional step comprising preparing the surface of the implanted device by a process chosen from the group comprising roughening and grooving.

4. The process of claim 1 wherein the step of applying the antimicrobial substance to the external surface of the implanted device is performed by a process of attaching an adhesive mixture of a proteinaceous or polymeric matrix and particles of an antimicrobial substance.

5. The process of claim 4 in which the particles of an antimicrobial substance comprise an oligodynamic metal.

6. The process of claim 4 in which the particles of an antimicrobial substance comprise taurolidine.

7. The process of claim 1 in which the antimicrobial substance comprises silver and the silver is applied by first applying an emulsion of silver halide to the exterior of the device, second exposing said emulsion to light, and third subjecting the emulsion to the reducing action of a photographic developer.

8. A process for disinfecting and rendering inhospitable to infections the space between an implanted device and the encapsulating tissue which forms around the device, said process comprising the steps of first partially withdrawing a needle from the implanted device and then flowing a solution comprising an antimicrobial substance into said space.

9. The process of claim 8 in which the implanted device is configured with an additional flow path hydraulically connected to a main flow path in the implanted device and opening into the pocket, said main flow path and said additional flow path being configured such that partial withdrawal of the needle opens the additional flow path into the pocket.

* * * * *